(12) United States Patent
Chuu et al.

(10) Patent No.: US 8,652,316 B1
(45) Date of Patent: Feb. 18, 2014

(54) ELECTROPHORESIS SYSTEM WITH PICTURE TAKING DEVICE

(71) Applicants: Wen-Liang Chuu, New Taipei (TW); Chian-Fu Wang, New Taipei (TW)

(72) Inventors: Wen-Liang Chuu, New Taipei (TW); Chian-Fu Wang, New Taipei (TW)

(73) Assignee: Major Science Co., Ltd., New Taipei (TW)

( * ) Notice: Subject to any disclaimer, the term of this patent is extended or adjusted under 35 U.S.C. 154(b) by 0 days.

(21) Appl. No.: 13/624,974

(22) Filed: Sep. 24, 2012

(51) Int. Cl.
*G01N 27/453* (2006.01)

(52) U.S. Cl.
USPC .......................................... 204/612; 204/616

(58) Field of Classification Search
USPC .................. 204/456, 461, 606, 612; 356/344; 382/128, 129
See application file for complete search history.

(56) References Cited

U.S. PATENT DOCUMENTS

| 5,449,446 A * | 9/1995 | Verma et al. ................... 204/612 |
| 5,774,214 A * | 6/1998 | Prettyjohns .................... 356/344 |
| 2005/0082168 A1* | 4/2005 | Kang ............................. 204/456 |

FOREIGN PATENT DOCUMENTS

WO    WO 88/05689 A1 *  8/1988 ............. B01D 13/02

* cited by examiner

*Primary Examiner* — Alex Noguerola

(57) ABSTRACT

An electrophoresis system includes a pedestal including a base, two enlargements at both ends of the base respectively, two cavities in the enlargements respectively, and a transparent plate on top of the base; a photographic filter member provided on the top of the base; a control panel on one enlargement; an electrophoresis tank provided between the enlargements; a covering member releasably provided on the pedestal for concealing the electrophoresis tank; a gel block in the electrophoresis tank for holding DNA samples in place; LED lamps in each cavity, the LED lamps being for emitting blue light toward the DNA samples; a hollow mount on the covering member and including a sliding tray; a photographic filter releasably disposed on the tray; and a picture taking device mounted on the hollow mount.

4 Claims, 16 Drawing Sheets

ELECTROPHORESIS SYSTEM WITH PICTURE TAKING DEVICE

BACKGROUND OF THE INVENTION

1. Field of the Invention

The invention relates to electrophoresis and more particularly to an electrophoresis system having a picture taking device.

2. Description of Related Art

Electrophoresis is used for a great number of applications. For example, electrophoresis is used for DNA sequencing to determine the genetic composition of a DNA sample. Many existing electrophoresis applications are undertaken using running tanks wherein a sample-containing gel is disposed in an electrophoresis tank in the running tank. Electric current is then applied to the gel by means of an electrode in the running tank to cause electrophoresis of the sample.

Typically, the electrophoresis tank is covered by a lid when energized. Otherwise, it may be unsafe for person operating the electrophoresis system due to radiation concerns. However, the typical safety arrangement is not reliable. Further, step details of the electrophoresis system in operation are not visually available. This means that a person performing the electrophoresis system is not aware of any errors occurred. As a result, successful electrophoresis cannot be ensured. Thus, the need for improvement still exists.

SUMMARY OF THE INVENTION

It is therefore one object of the invention to provide an electrophoresis system comprising a pedestal comprising a base, two enlargements at both ends of the base respectively, two cavities provided in the enlargements respectively, and a transparent plate provided on a top of the base; a photographic filter member provided on the top of the base; a control panel provided on one enlargement; an electrophoresis tank provided between the enlargements; a covering member releasably provided on the pedestal for concealing the electrophoresis tank; a gel block provided in the electrophoresis tank for holding a plurality of DNA samples in place; a plurality of LED lamps provided in each of the cavities, the LED lamps being for emitting blue light toward the DNA samples; a hollow mount provided on the covering member and comprising a tray slidably disposed in the hollow mount, and a photographic filter releasably disposed on the tray; and a picture taking device mounted on the hollow mount.

The above and other objects, features and advantages of the invention will become apparent from the following detailed description taken with the accompanying drawings.

DETAILED DESCRIPTION OF THE INVENTION

Figure 1:
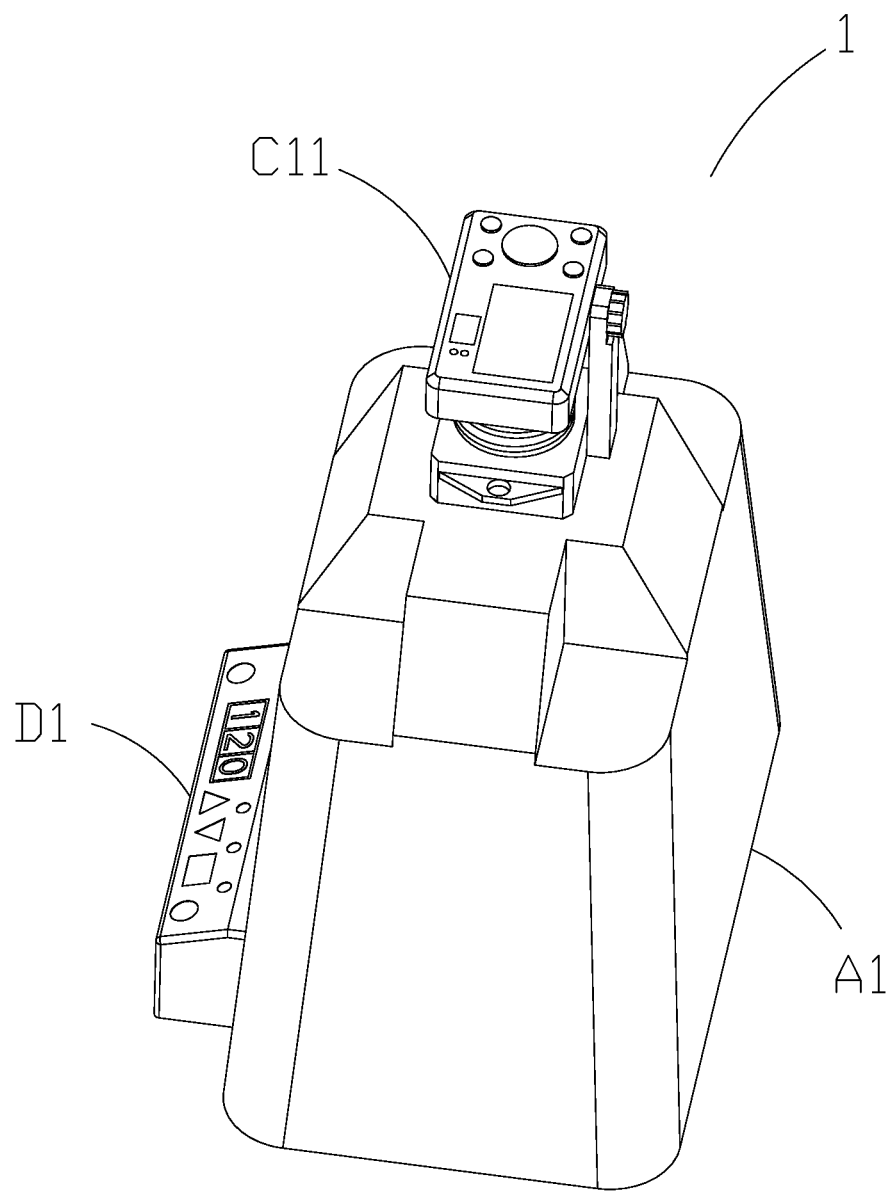
FIG. 1 is a perspective view of an electrophoresis system with a picture taking device according to a first preferred embodiment of the invention.
Figure 2:
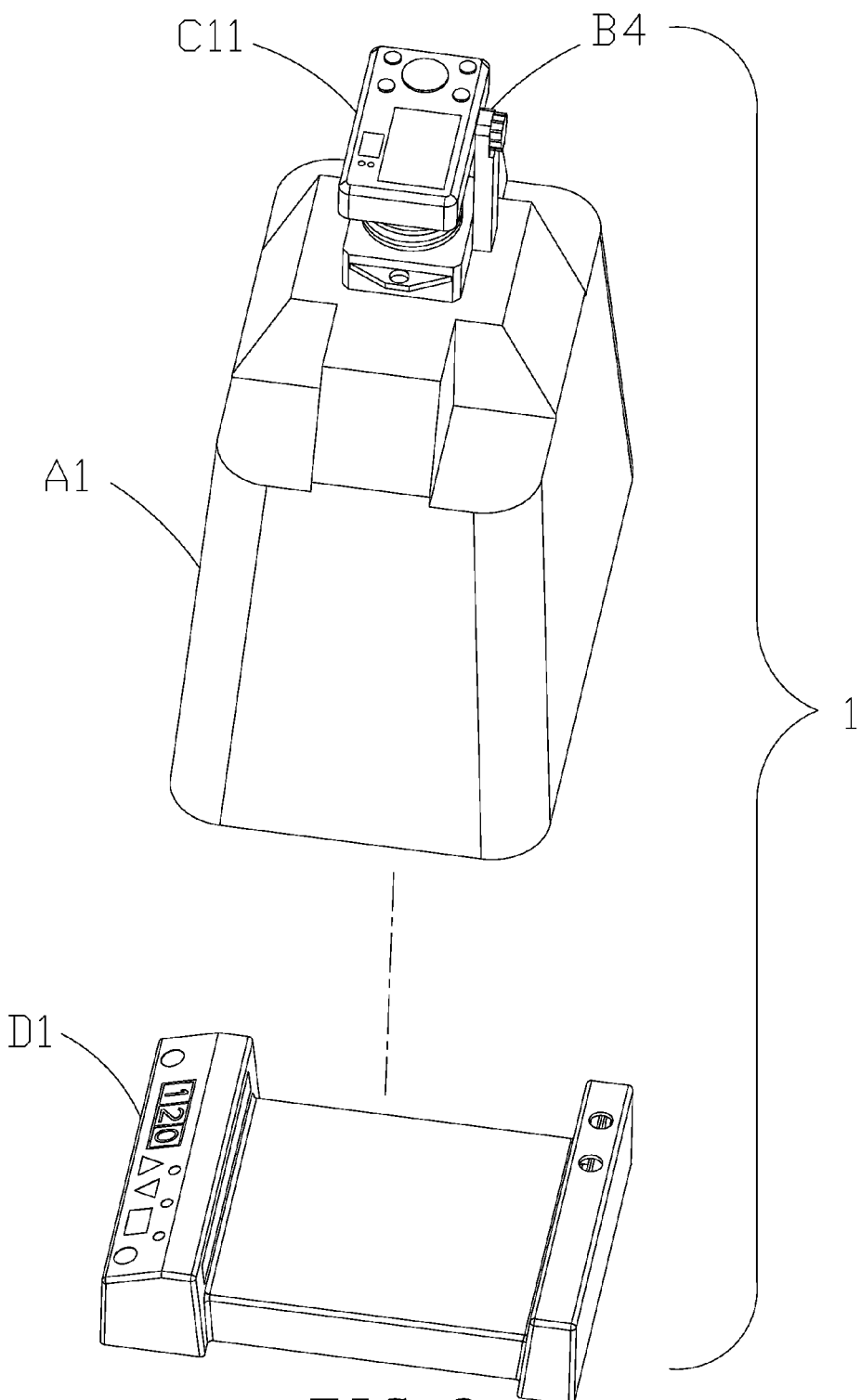
FIG. 2 is an exploded view of FIG. 1 with a pedestal separated.
Figure 3:
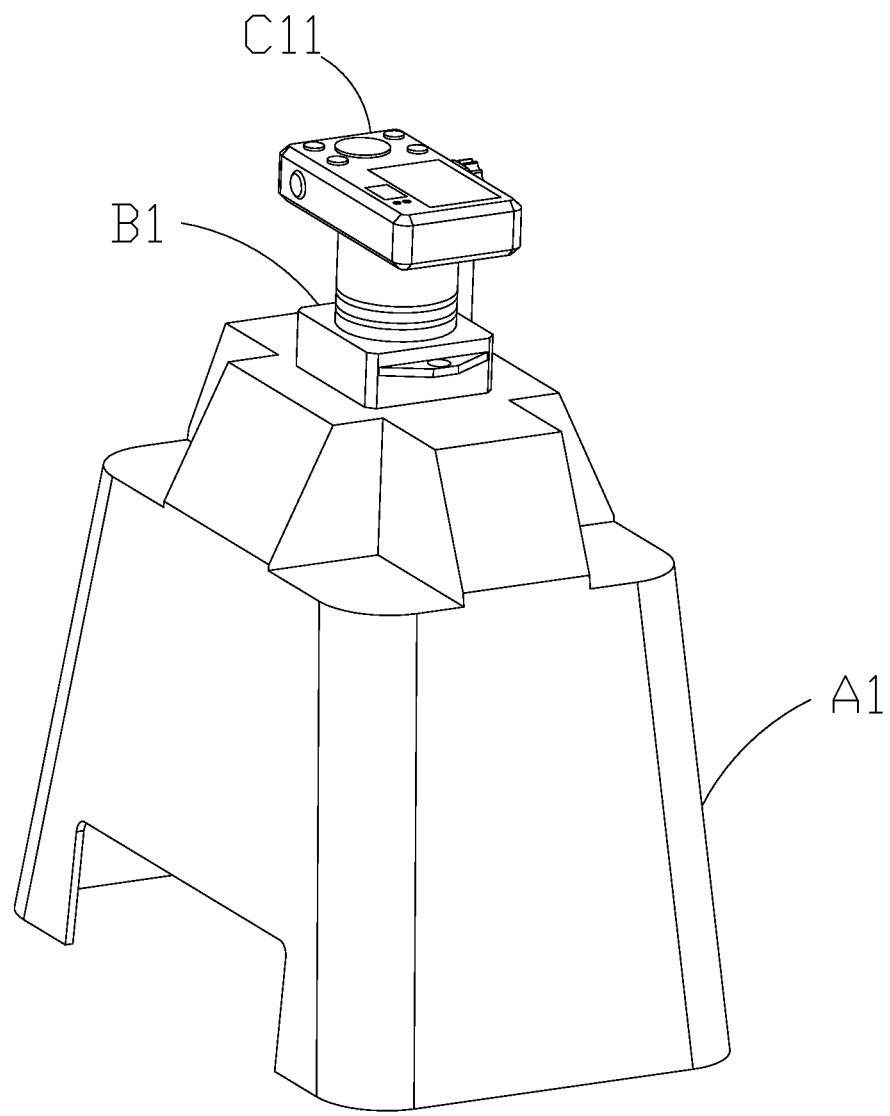
FIG. 3 is a perspective view of a covering member, a hollow mount and a digital camera of FIG. 2.
Figure 4:
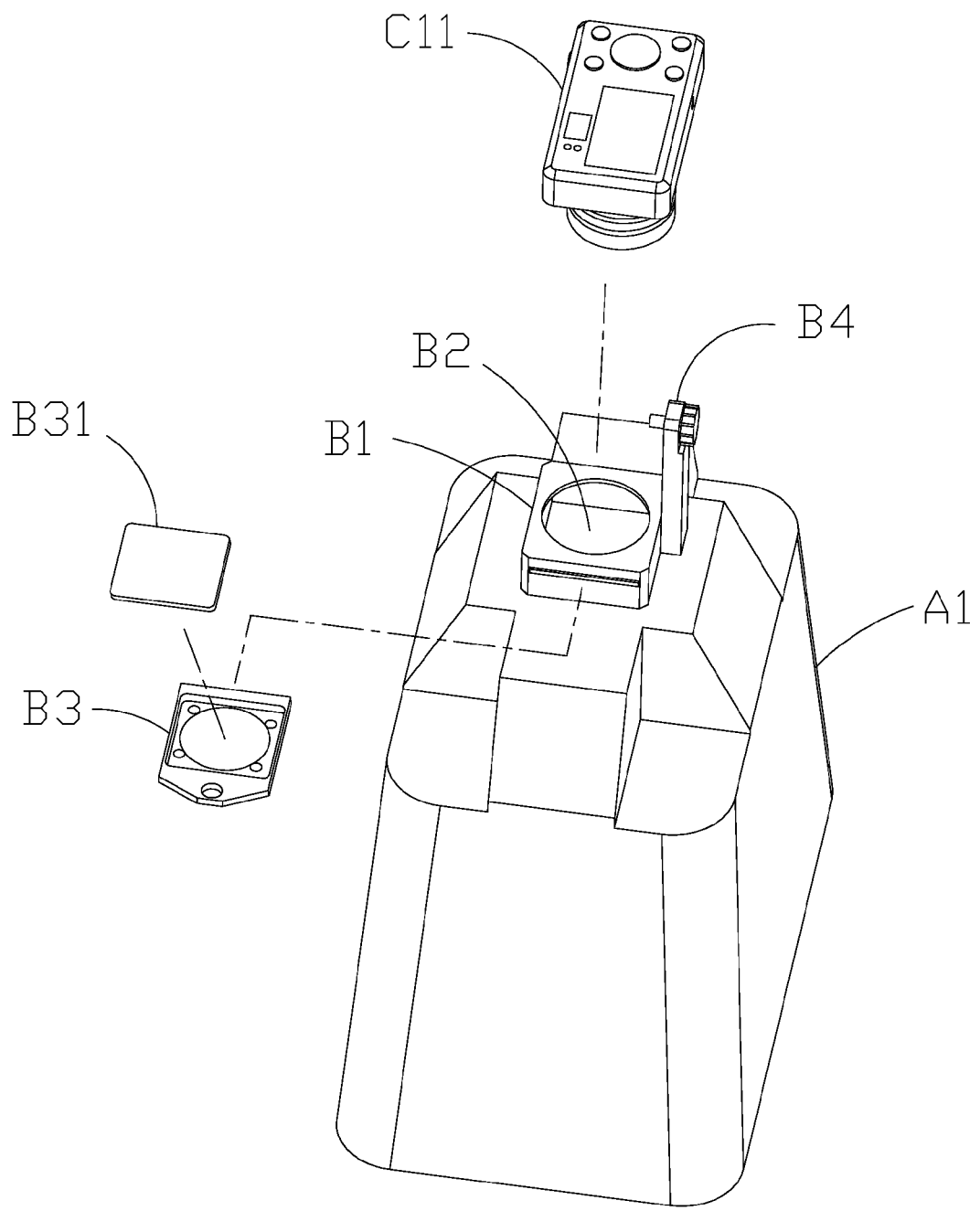
FIG. 4 is an exploded view of FIG. 3.
Figure 5:
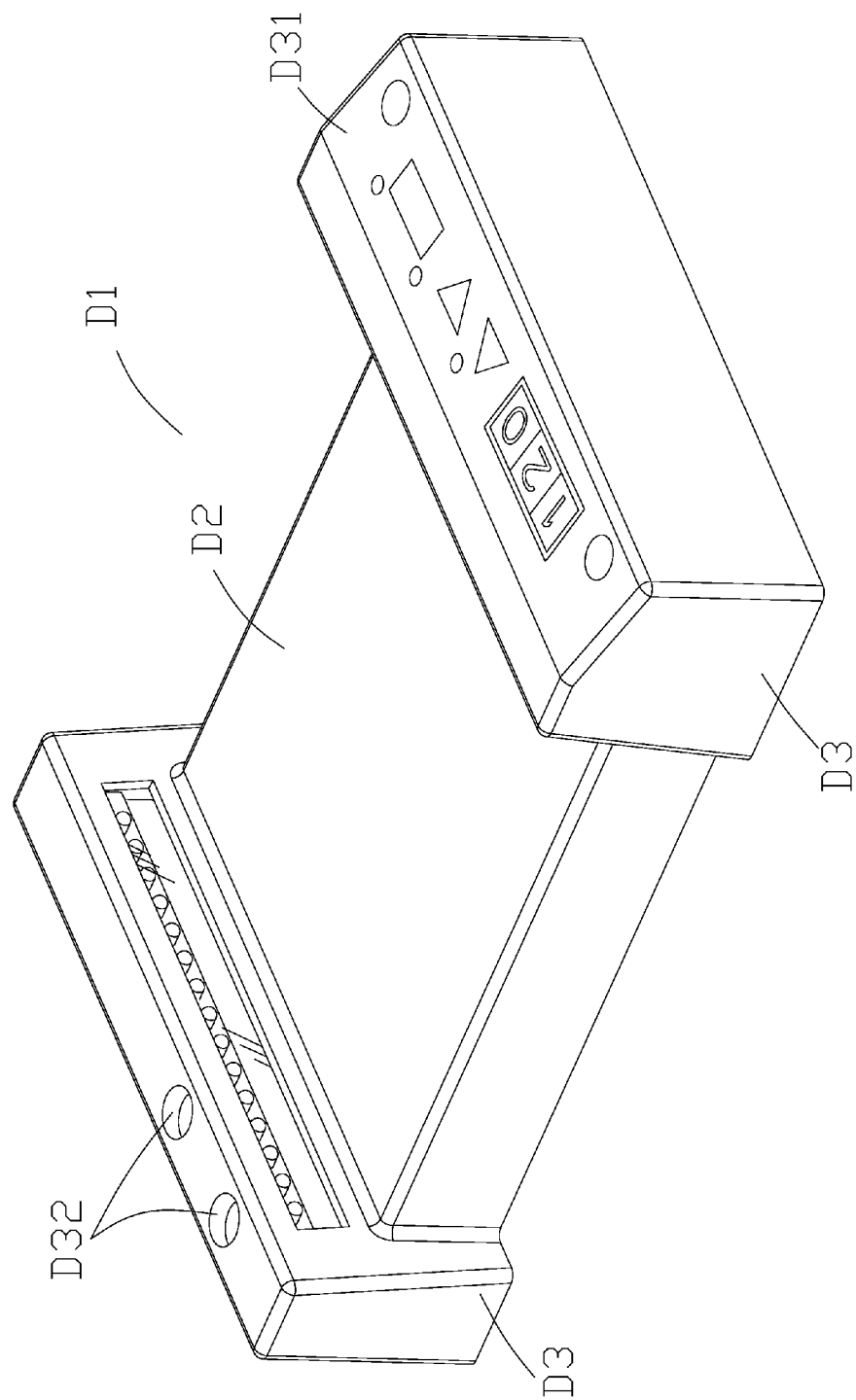
FIG. 5 is a perspective view of the pedestal.
Figure 6:
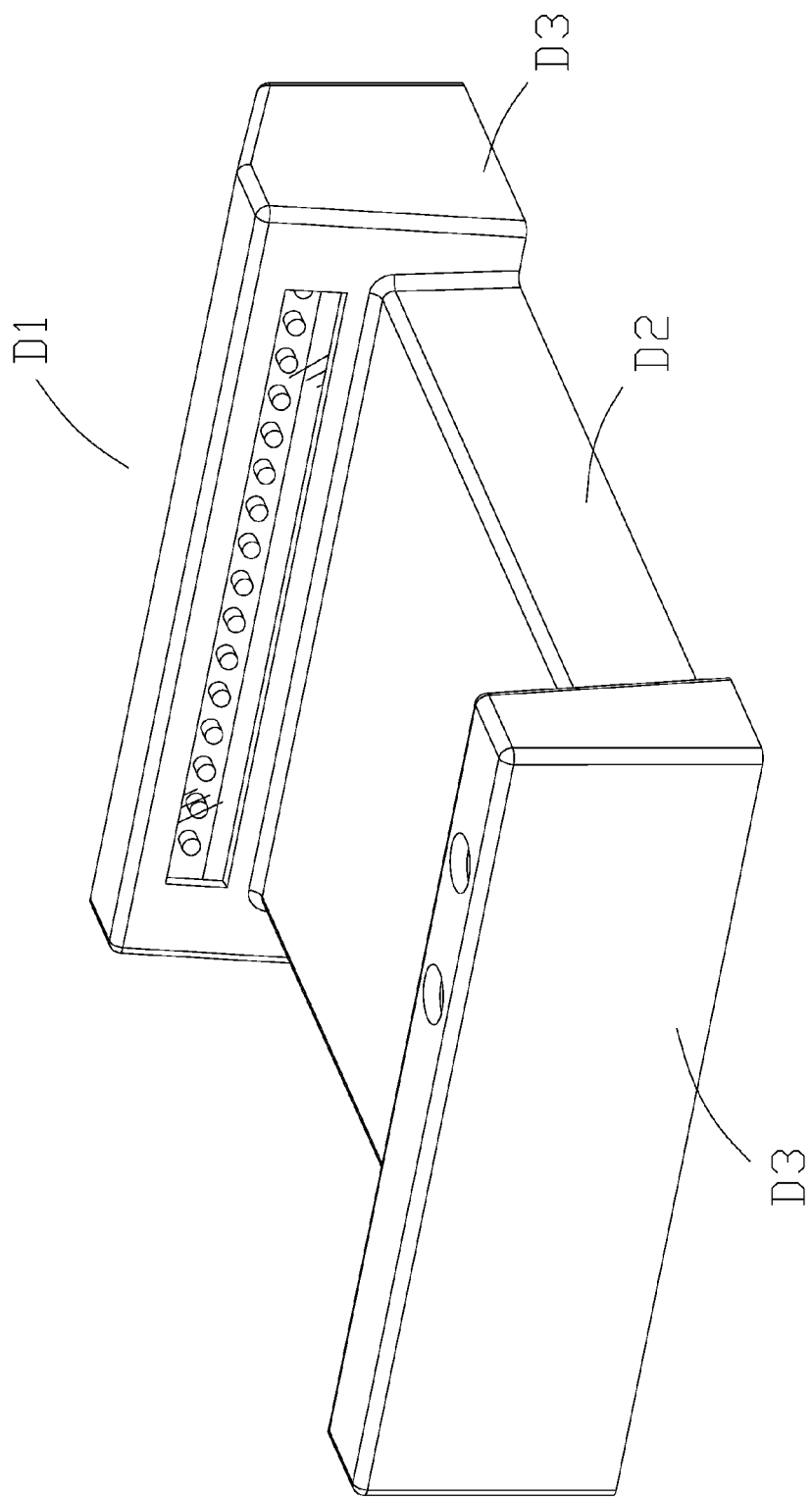
FIG. 6 is another perspective view of the pedestal.
Figure 7:
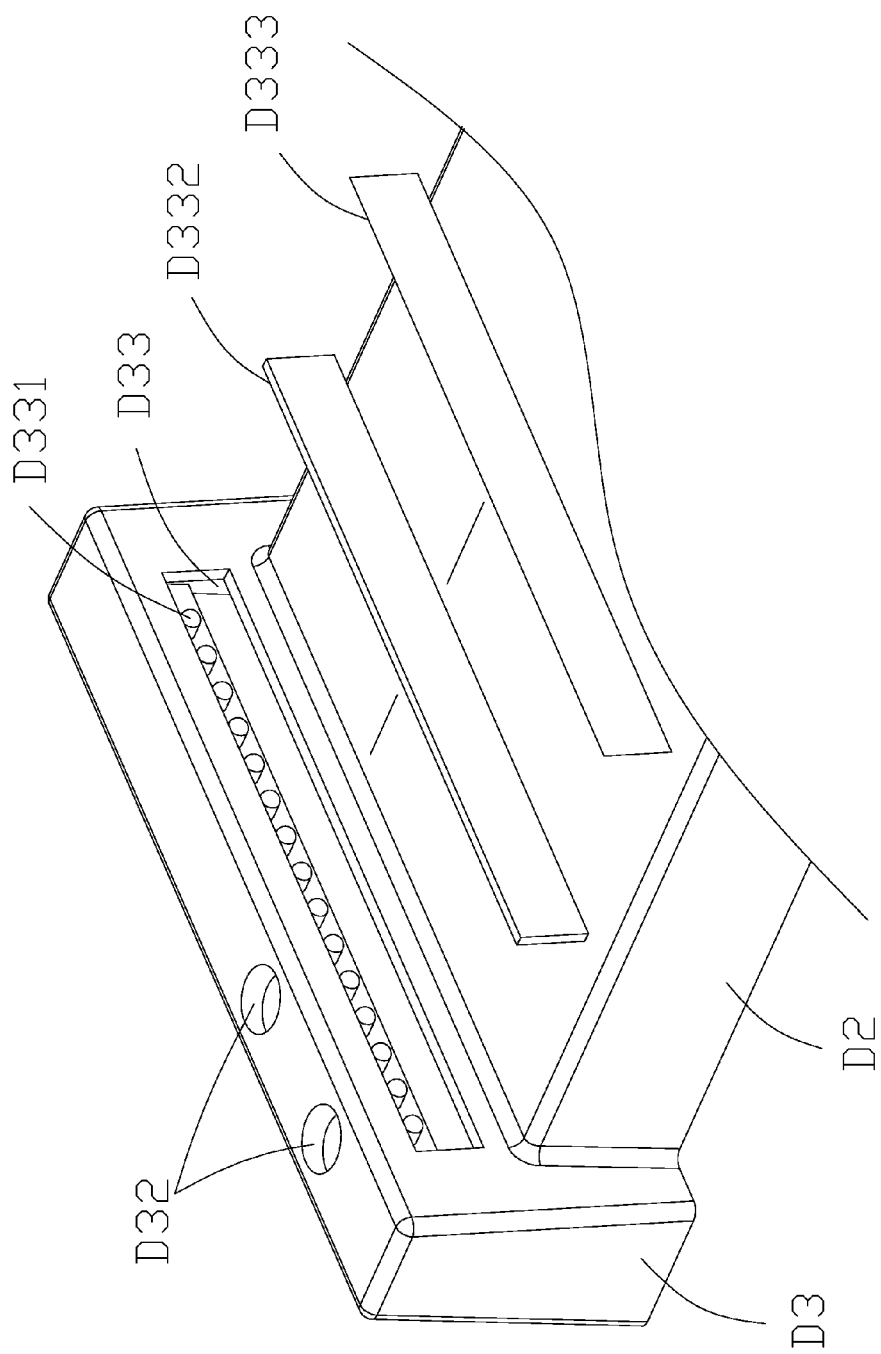
FIG. 7 is a fragmentary view of FIG. 5 with a second photographic filter and a transparent plate mounted on the base.
Figure 8:
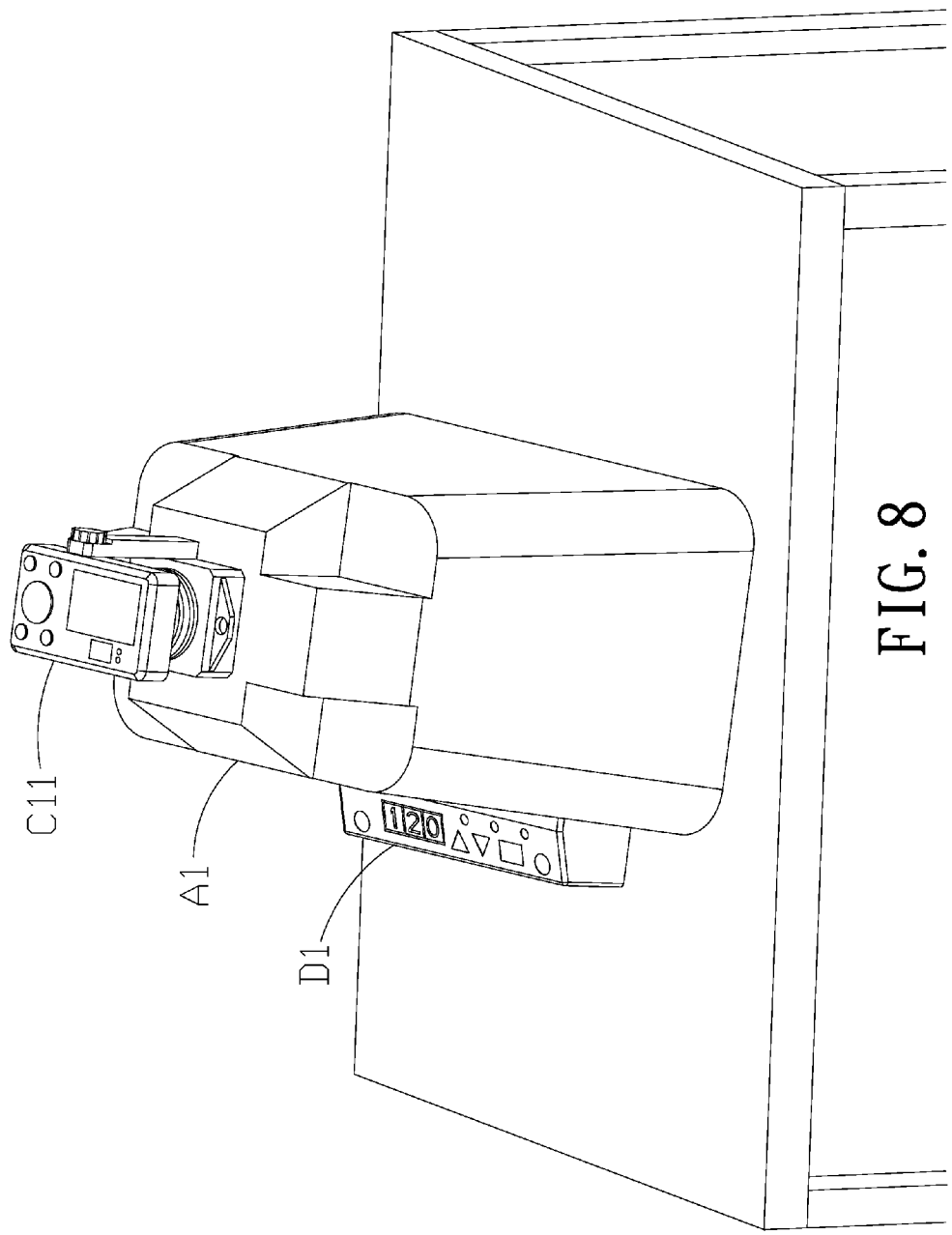
FIG. 8 is a perspective view of the picture taking device on a table.
Figure 9:
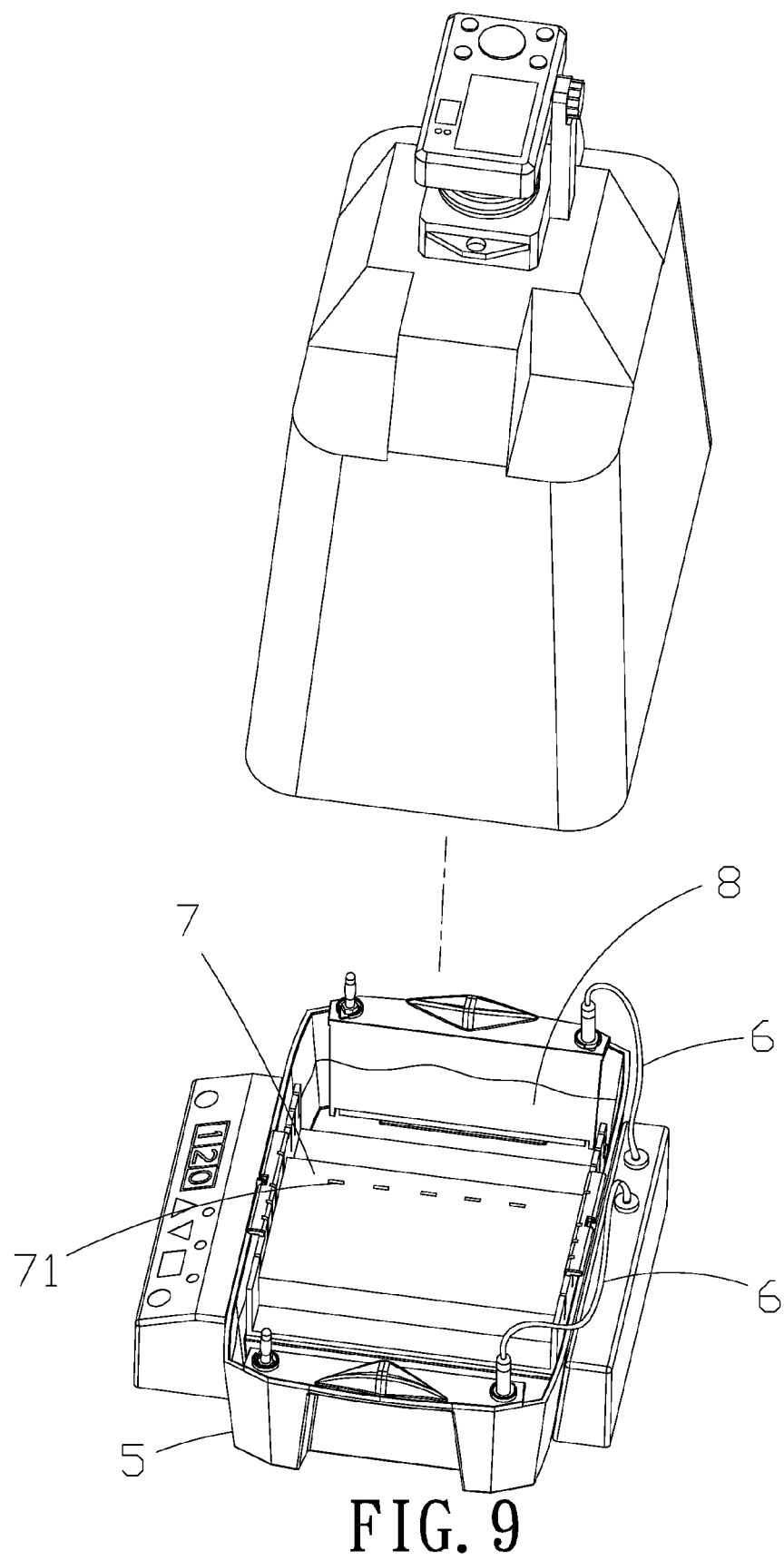
FIG. 9 is an exploded view similar to FIG. 2 showing an electrophoresis tank mounted on the base.
Figure 10:
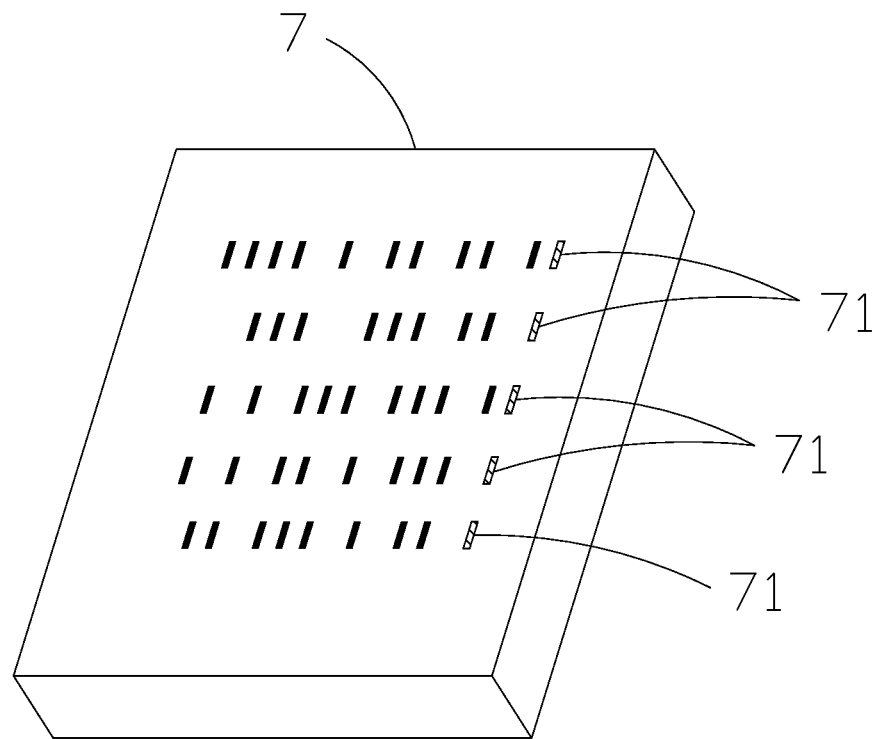
FIG. 10 is a perspective view of DNA samples on top of a gel block of FIG. 9.

Referring to FIGS. 1 to 10, a picture taking device 1 for electrophoresis system accordance with a first preferred embodiment of the invention comprises the following components as discussed in detail below.

A pedestal D1 is provided and a covering member A1 is releasably provided on the pedestal D1. A hollow mount B1 is provided on top of the covering member A1 and comprises a top opening B2, a sliding tray B3 adapted to insert into the hollow mount B1, a first photographic filter B31 adapted to place on the tray B3, and a support B4 projecting upward from one side of the hollow mount B1. A digital camera C11 has a lower portion inserted into the hollow mount B1 through the opening B2 and is secured by the support B4.

The pedestal D1 has a longitudinal section of U and comprises a rectangular base D2, two enlargements D3 at both ends of the base D2 respectively. A power supply (not shown) is mounted in the base D2. A cavity D33 is provided on an inner surface of each enlargement D3. A plurality of light-emitting diode (LED) lamps D331 for emitting blue light are provided in the cavity D33. A rectangular transparent plate D332 is provided on top of the base D2 and parallel to the enlargements D2. A rectangular second photographic filter D333 is provided on the top of the base D2 and parallel to the transparent plate D332. A control panel D31 powered by the power supply is provided on an inclined top of one enlargement D3. Two openings D32 are provided on a top of the other enlargement D3.

An electrophoresis tank 5 is provided between the enlargements on the base D2 and has electrophoresis electrodes electrically connect to the pedestal D1 by wiring 6 through the openings D32 (i.e., being powered by the power supply). A gel block 7 is provided on a rectangular top recess of the electrophoresis tank 5 and has a fluorescent dye adapted to be excited by the blue light emitted by the LED lamps D331. A plurality of Deoxyribonucleic acid (DNA) samples 71 are provided on top of the gel block 7 in rows. State changes of the DNA samples 71 can be visually observed by watching the color change of the fluorescent dye in the electrophoresis system. The second photographic filter D333 can eliminate light outer than the blue light out of the illumination of the LED lamps D331 because only blue light is necessary for the excitation of the fluorescent dye.

The covering member A1 is secured onto the electrophoresis tank 5 for covering so that the color change of the fluorescent dye of the gel block 7 can be seen clearly for determining whether there are state changes of the DNA samples 71. The provision of the second photographic filter D333 can further ensure correctness of the determination. Lens of the digital camera C11 is disposed in the hollow mount B1 to face the first photographic filter B31 through the opening B2. In the electrophoresis system, a person may view the DNA samples 71 through the lens of the digital camera C11 and further take a picture of the DNA samples 71 as record. Furthermore, the person may immediately stop the electrophoresis system if there is any error. As a result, a successful electrophoresis system can be ensured.

Figure 11:
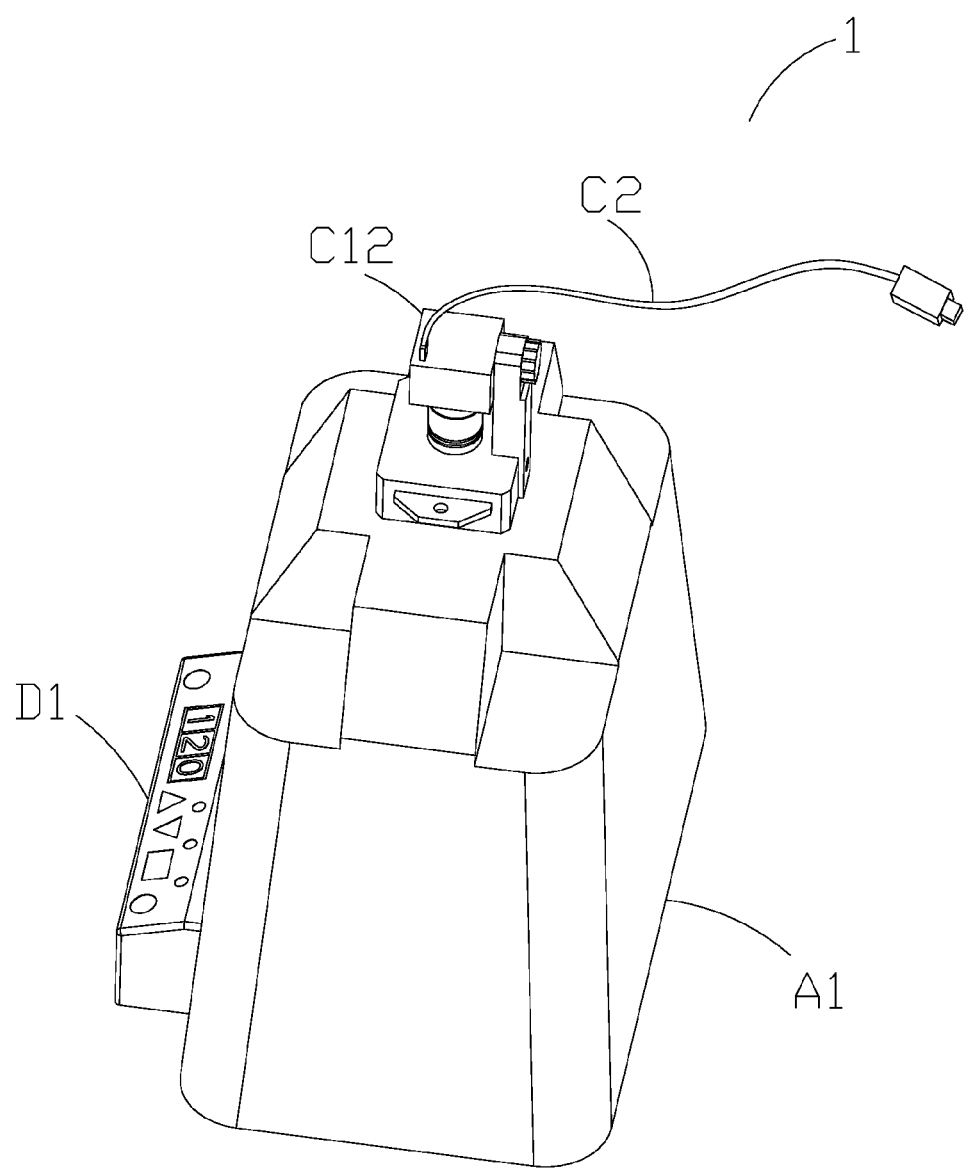
FIG. 11 is a perspective view of an electrophoresis system with a picture taking device according to a second preferred embodiment of the invention.
Figure 12:
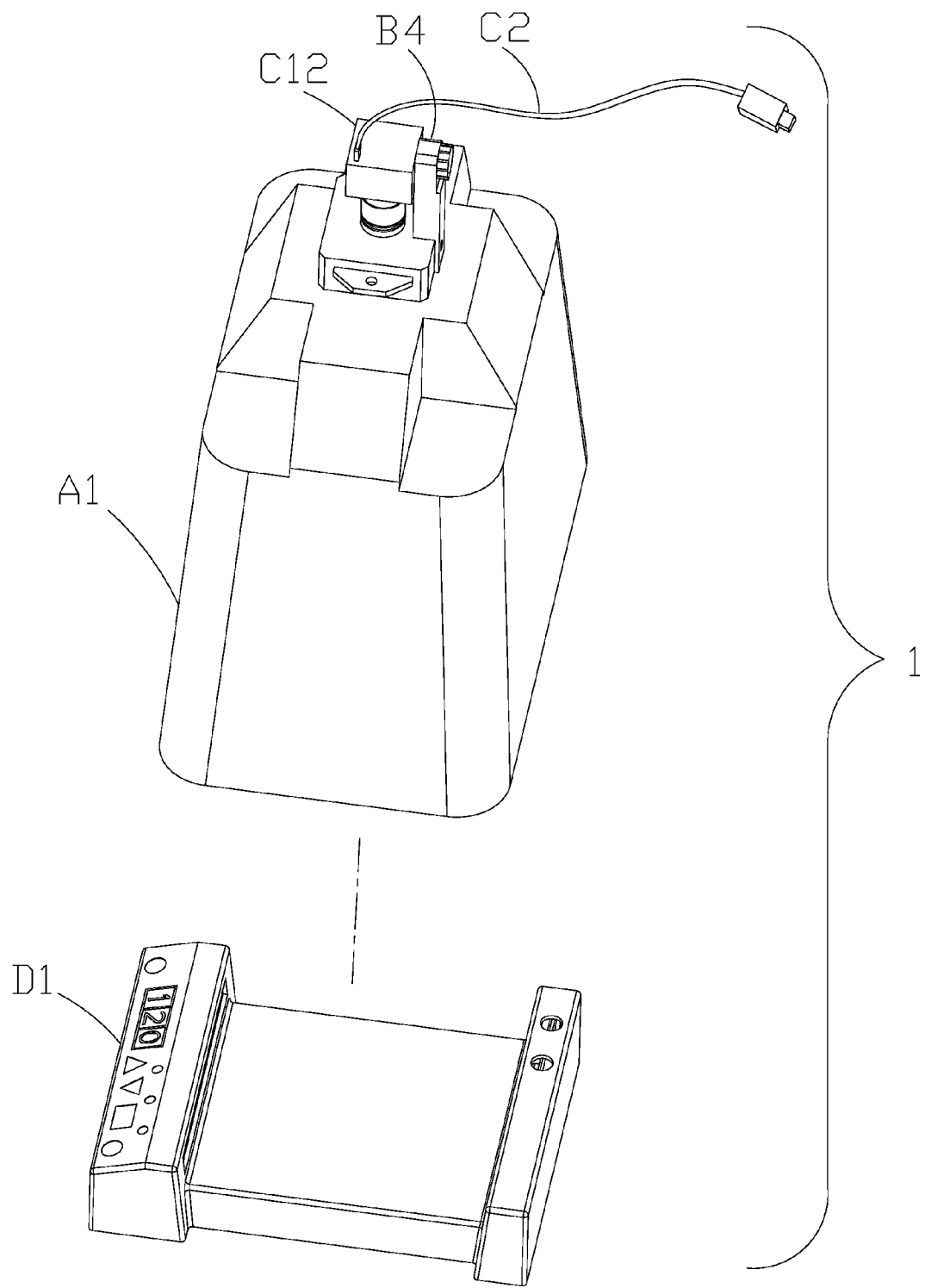
FIG. 12 is an exploded view of FIG. 11 with a pedestal separated.
Figure 13:
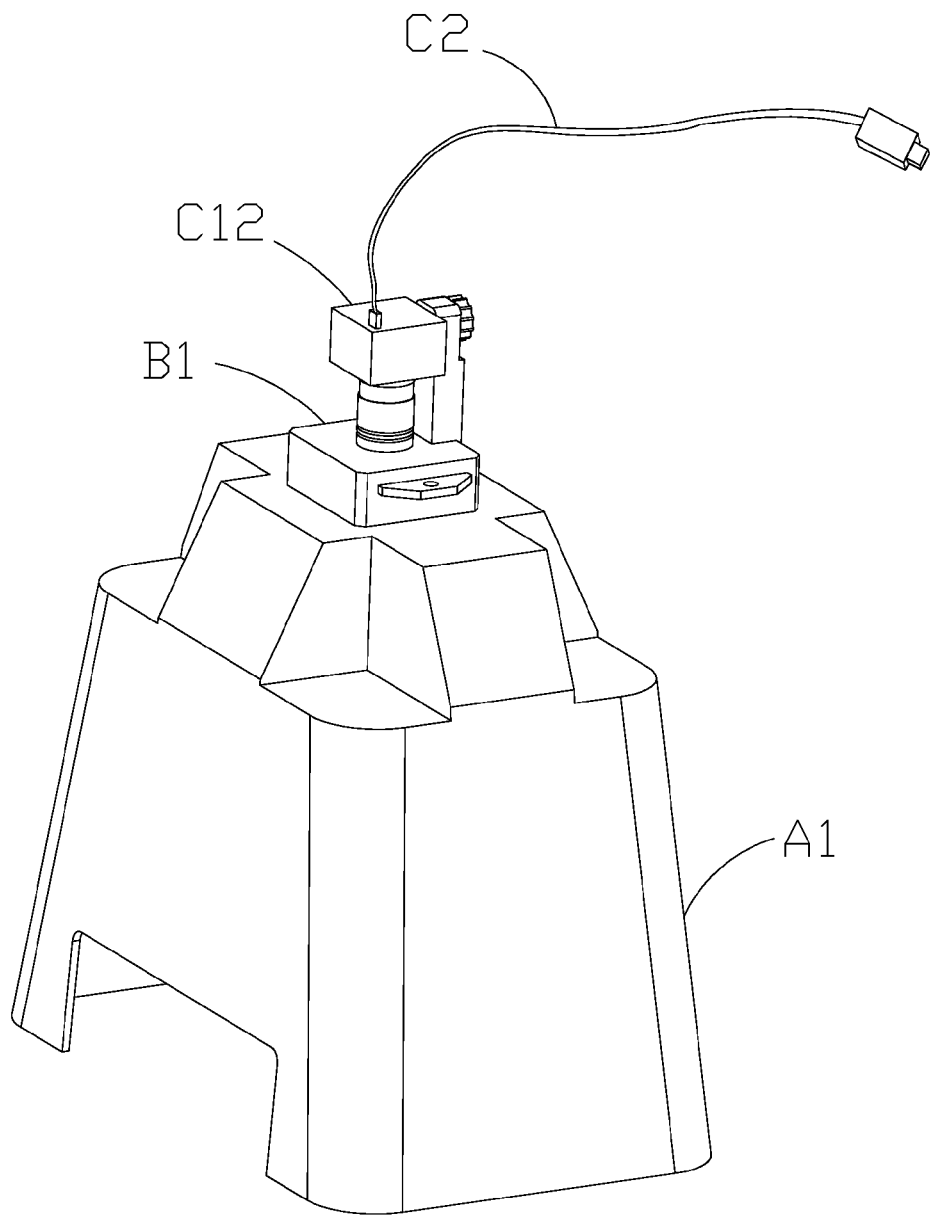
FIG. 13 is a perspective view of a covering member, a hollow mount and a camera member of FIG. 12.
Figure 14:
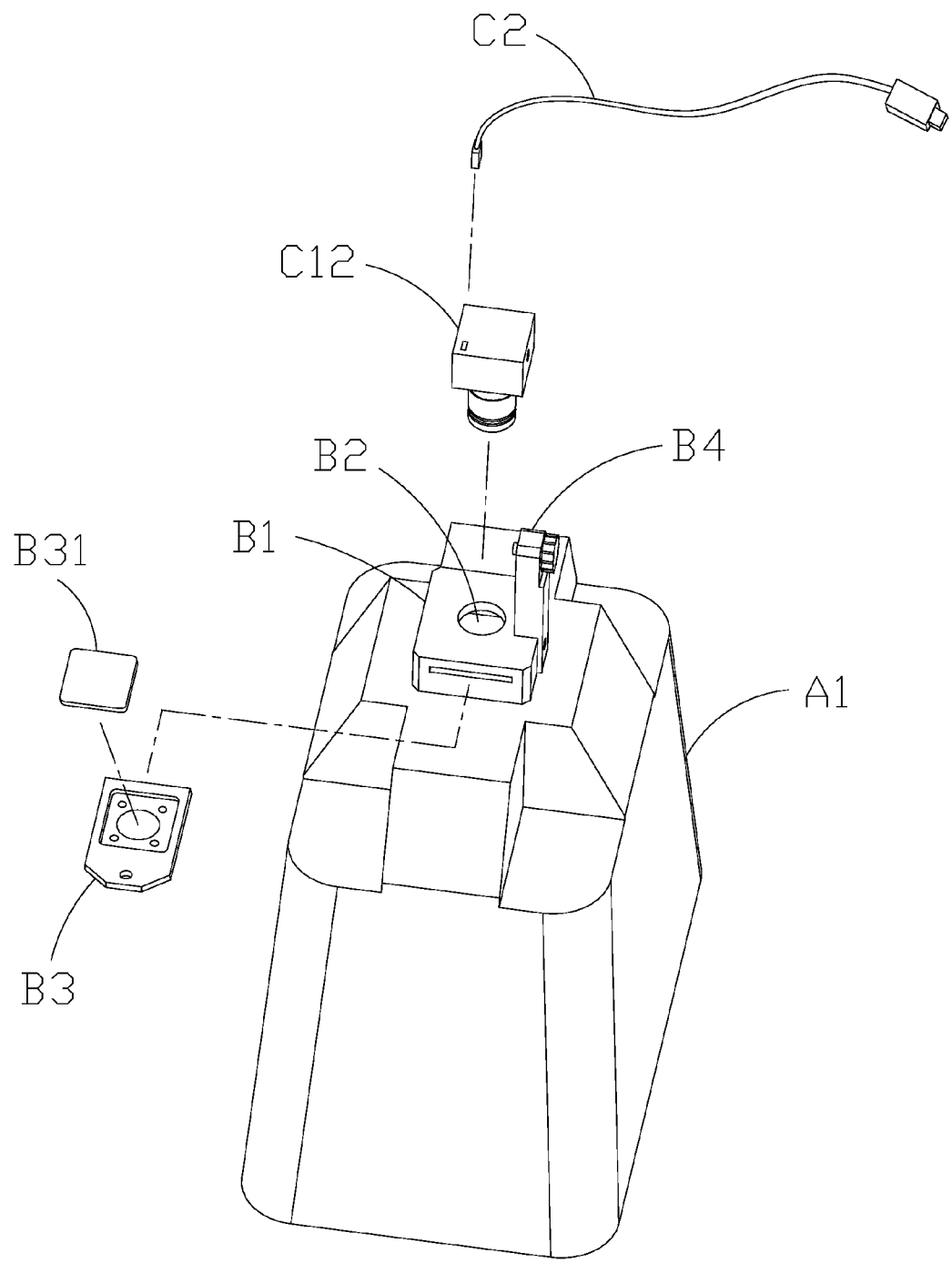
FIG. 14 is an exploded view of FIG. 13.
Figure 15:
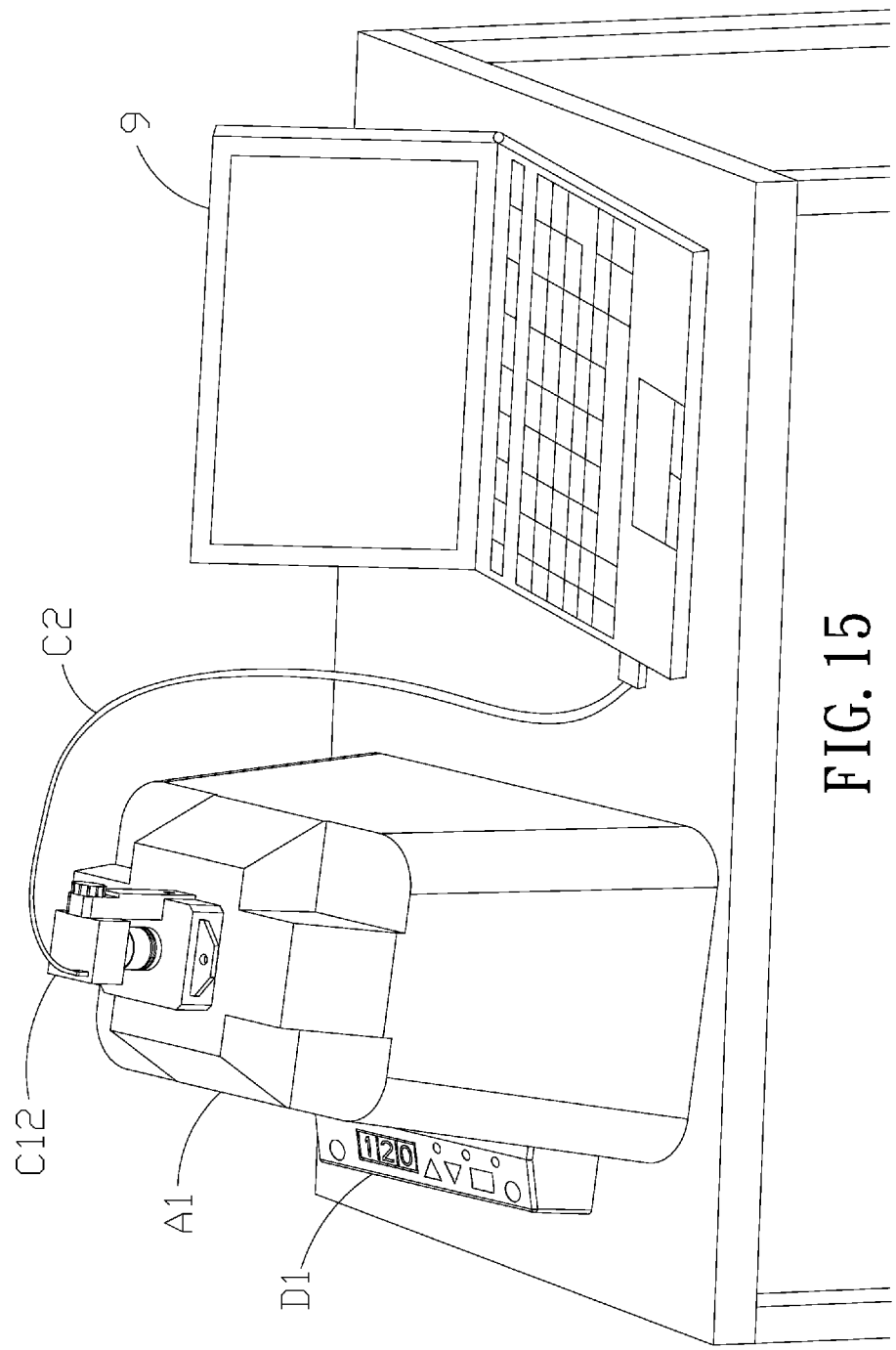
FIG. 15 is a perspective view of the picture taking device and a laptop computer connected to the picture taking device on a table.
Figure 16:
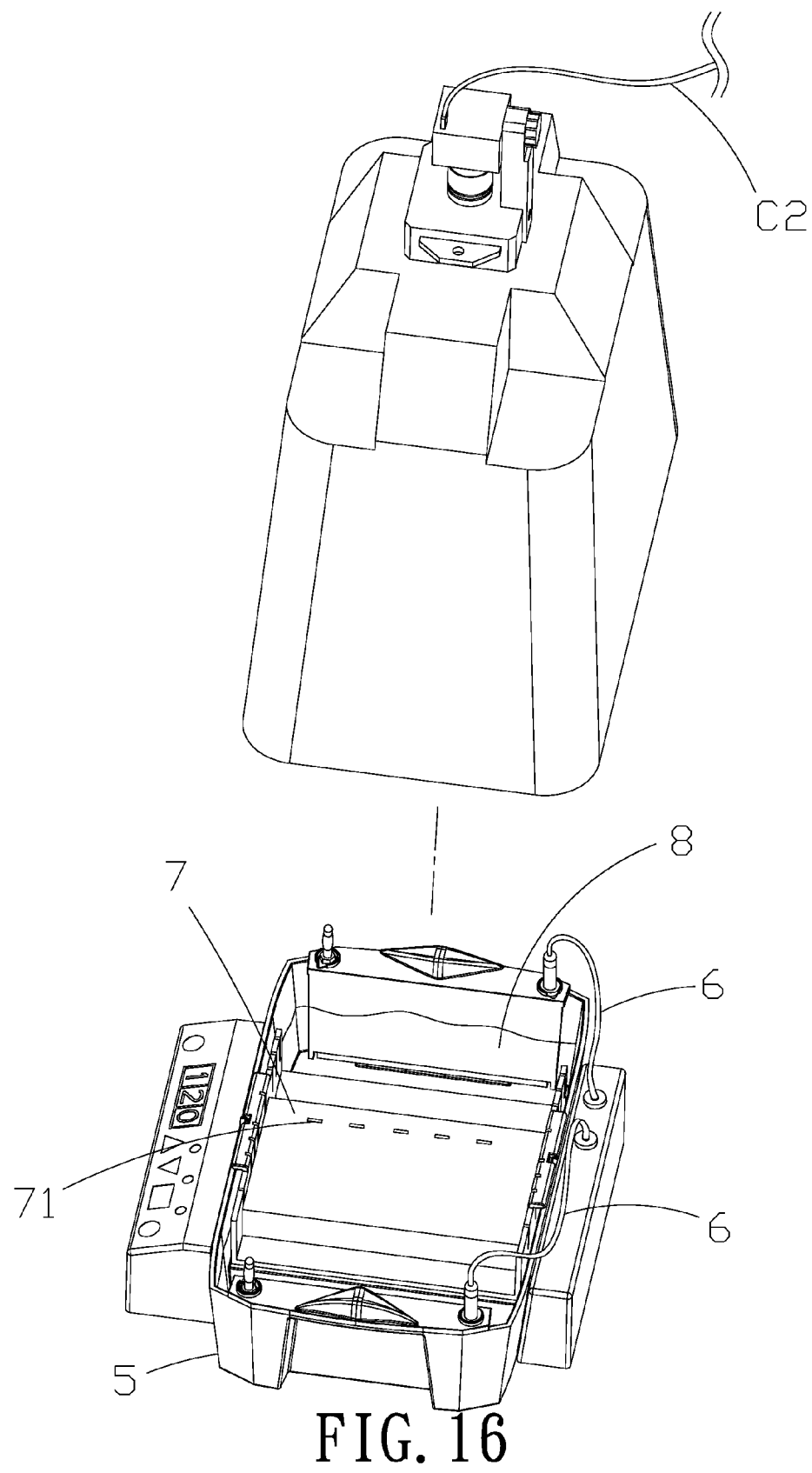
FIG. 16 is an exploded view similar to FIG. 12 showing an electrophoresis tank mounted on the base.

Referring to FIGS. 11 to 16, a picture taking device 1 for electrophoresis system in accordance with a second preferred embodiment of the invention is shown. The characteristics of the second preferred embodiment are substantially the same as that of the first preferred embodiment except the following:

The digital camera of the second preferred embodiment is replaced with a camera member C12 implemented as a complementary-metal-oxide-semiconductor (CMOS) image sensor or a charge-coupled device (CCD) image sensor. Further, a Universal Serial Bus (USB) cable C2 is provided to connect the camera member C12 to a laptop computer 9. In short, a person operating the picture taking device 1 can understand the step details of the electrophoresis system by watching what is shown on the screen of the laptop computer 9 in a relatively easy manner.

While the invention has been described in terms of preferred embodiments, those skilled in the art will recognize that the invention can be practiced with modifications within the spirit and scope of the appended claims.

What is claimed is:
1. An electrophoresis system comprising:
 a pedestal comprising a base having two ends and a top, an enlargement at each end of the base, a cavity in each enlargement, and a transparent plate disposed on the top of the base;
 a photographic filter member disposed on the top of the base;
 a control panel disposed on one enlargement;
 an electrophoresis tank disposed on the base between the enlargements;
 a covering member releasably disposed on the pedestal for concealing the electrophoresis tank;
 a gel block disposed in the electrophoresis tank for holding a plurality of Deoxyribonucleic acid (DNA) samples in place;
 a plurality of light-emitting diode (LED) lamps disposed in each of the cavities, the LED lamps being for emitting blue light toward the DNA samples;
 a hollow mount disposed on the covering member and comprising a sliding tray;
 a photographic filter releasably disposed on the tray; and
 a picture taking device mounted on the hollow mount.
2. The electrophoresis system of claim 1, wherein the picture taking device is a digital camera.
3. The electrophoresis system of claim 1, wherein the picture taking device is a CMSO image sensor.
4. The electrophoresis system of claim 1, wherein the picture taking device is a CCD mage sensor.

\* \* \* \* \*